United States Patent
Mandrea (10) Patent No.: US 7,893,083 B2
(45) Date of Patent: Feb. 22, 2011

(54) METHOD OF TREATING GENITAL HERPES

(76) Inventor: Eugene Mandrea, 7300 College Dr., Palos Heights, IL (US) 60463

( * ) Notice: Subject to any disclaimer, the term of this patent is extended or adjusted under 35 U.S.C. 154(b) by 96 days.

(21) Appl. No.: 12/113,833

(22) Filed: May 1, 2008

(65) Prior Publication Data

US 2008/0269274 A1   Oct. 30, 2008

Related U.S. Application Data (63) Continuation-in-part of application No. 11/318,659, filed on Dec. 21, 2005, now abandoned, which is a continuation-in-part of application No. 11/109,553, filed on Apr. 19, 2005, now abandoned, which is a continuation-in-part of application No. 10/751,371, filed on Jan. 5, 2004, now abandoned.

(60) Provisional application No. 60/438,431, filed on Jan. 6, 2003.

(51) Int. Cl.
*A01N 43/42* (2006.01)
*A61K 39/00* (2006.01)
*A61K 39/245* (2006.01)

(52) U.S. Cl. .................. 514/293; 424/229.1; 424/231.1

(58) Field of Classification Search .................. 514/293
See application file for complete search history.

(56) References Cited

U.S. PATENT DOCUMENTS

| | | | |
|---|---|---|---|
| 3,608,065 A * | 9/1971 | Lover et al. | 424/45 |
| 6,039,969 A * | 3/2000 | Tomai et al. | 424/434 |
| 6,147,086 A | 11/2000 | Brenman | |
| 6,245,776 B1 | 6/2001 | Skwierczynski et al. | |
| 6,361,769 B1 | 3/2002 | Tovey | |
| 6,491,940 B1 * | 12/2002 | Levin | 424/434 |
| 6,569,435 B1 | 5/2003 | Punnonen et al. | |
| 6,576,757 B1 | 6/2003 | Punnonen et al. | |
| 6,890,904 B1 | 5/2005 | Wallner et al. | |

(Continued)

OTHER PUBLICATIONS

Arrese, Jorge E., et al., "Dermal Dendritic Cells in Anogenital Warty Lesions Unresponsive to an Immune-Response Modifier," 2001, pp. 131-134, Journal of Cutaneous Pathology, vol. 28.

(Continued)

*Primary Examiner*—San-ming Hui
*Assistant Examiner*—Kathrien Cruz
(74) *Attorney, Agent, or Firm*—James P. Muraff; Neal, Gerber & Eisenberg LLP (57) ABSTRACT

The present invention is directed to a method of increasing the time period between outbreaks of genital herpes comprising providing an imidazoquinolinamine formulation, disposing an amount of the imidazoquinolinamine formulation into a first nare of an individual infected with Herpes Simplex Virus type 2, covering at least a portion of the internal surface of the individual's first nare with a portion of the amount of the imidazoquinolinamine in the nare, massaging the portion of the amount of the imidazoquinolinamine into the internal surface of the first nare, disposing the amount of the imidazoquinolinamine formulation into a second nare of the individual, covering at least a portion of the internal surface of the second nare with a portion of the amount of the imidazoquinolinamine in said nare and massaging the portion of the amount of the imidazoquinolinamine into the internal surface of said nare.

13 Claims, 6 Drawing Sheets

U.S. PATENT DOCUMENTS

| | | | |
|---|---|---|---|
| 2003/0139364 A1* | 7/2003 | Krieg et al. | 514/44 |
| 2004/0067953 A1 | 4/2004 | Stein et al. | |
| 2004/0136917 A1 | 7/2004 | Mandrea | |

OTHER PUBLICATIONS

Bishop, Gail A., "The Immune Response Modifier Resiquimod Mimics CD40-Induced B Cell Activation," Mar. 8, 2001, pp. 9-17, Cellular Immunology, vol. 208, Academic Press.

Dahl, Mark V., "Imiquimod: A Cytokine Inducer," Oct. 2002, pp. S205-S208, J. Am. Acad. Dermatol., vol. 47, No. 4, American Academy of Dermatology, Inc.

Dockrell, D. H., Imiquimod and Resiquimod as Novel immunomodulators, 2001, pp. 751-755, Journal of Antimicrobial Chemotherapy, vol. 48, The British Society for Antimicrobial Chemotherapy.

Gibson, Sheila J., et al., "Plasmacytoid Dendritic Cells Produce Cytokines and Mature in Response to the TLR7 Agonists, Imiquimod and Resiquimod," 2002, pp. 74-86, Cellular Immunology, vol. 218, Elsevier Science, USA.

Hemmi, Hiroaki, et al., "Small Anti-Viral Compounds Activate Immune Cells Via the TLR7 MyD88-Dependent Signaling Pathway," Jan. 22, 2002, pp. 196-200, Nature Immunology, vol. 3, No. 2, Nature Publishing Group.

O'Mahony, C., et al., "New Patient-Applied Therapy for Anogenital Warts is Rate Favourably by Patients," Sep. 2001, pp. 565-570, International Journal of STD & AIDS, vol. 12.

Stanley, M. A., "Imiquimod and the Imidazoquinolones: Mechanism of Action and Therapeutic Potential," 2002, pp. 571-577, Clinical and Experimental Dermatology, vol. 27, Blackwell Science Ltd.

Clejan, Sanda, et al., "Immune Responses Induced by Intranasal Imiquimod and Implications for Therapeutics in Rhinovirus Infections," 2005, pp. 457-461, J. Cell, Mol. Med., vol. 9, No. 2.

Gaspari, Anthony A., et al., "Immunotherapy of Basal Cell Carcinoma: Evolving Approaches," Oct. 2003, pp. 1027-1034, American Society for Dermatologic Surgery, Inc., vol. 29, No. 10, Blackwell Publishing, Inc.

Goodman and Gilman's The Pharmacological Basis of Therapeutics, 7th Edition, pp. 170-171, 2007.

Hendeles (Abstract, Selecting a Decongestant, Pharmacotherapy, Nov./Dec. 1993, 13, pp. 129S-134S).

C.J Harrison et al., "Modification of Immunological Responses and Clinical Disease During Topical R-837 Treatment of Genital HSV-2 Infection," Antiviral Research, 10 (1988), pp. 209-223.

Kathleen J. Smith et al., "Squamous Cell Carcinoma in Situ (Bowen's Disease) in Renal Transplant Patients Treated with 5% Imiquimod and 5% 5-Fluorouracil Therapy,", Dermatol Surg 2001; 27: pp. 561-564.

Nuria Verdaguer et al., "X-ray Structure of a Minor Group Human Rhinovirus Bound to a Fragment of its Cellular Receptor Protein," Nature Structural & Molecular Biology, vol. 11, No. 5, May 2004, pp. 429-434.

"Correspondence," British Journal ofDermatology 2002: 146: pp. 331-344.

E. Stockfleth et al., "Successful Treatment of Actinic Keratosis with Imiquimod Cream 5%: a Report of Six Cases," British Journal of Dermatology 2001: 144: pp. 1050-1053.

Alicia R. Barba, "An Open Label Safety Study of Topical Imiquimod 5% Cream in the Treatment of Molluscum Contagiosum in Children," Dermatology Online Journal, Jun. 25, 2006, vol. 7, No. 1, pp. 1-6.

Theresa L. Schroeder, "Squamous Cell Carcinoma in Situ of the Penis Successfully Treated with Imiquimod 5% Cream," J Am Acad Dermatol, Apr. 2002, vol. 46, No. 4, pp. 545-548.

Robin Marks, "Imiquimod 5% Cream in the Treatment of Superficial Basal Cell Carcinoma: Results of a Multicenter 6-Week Dose-Response Trial," J Am Acad Dermatol, May 2001, vol. 44, No. 5, pp. 807-813.

Claus Oster-Schmidt, "Imiquimod: A New Possibility for Treatment-Resistant Verrucae Planae," Arch Dermatol, vol. 137, May 2001, pp. 666-667.

Abstracts, The Journal of Investigative Dermatology, p. 584, Oct. 1989.

SJ Gibson et al., "Oral R-837 Induces a Interferon in Cynomologus Mon," Journal of Interferon Research, vol. 10, issue Suppl. 1, 1990, p. S124.

Michael J. Reiter, et al., "Cytokine Induction in Mice by the Immunomodulator Imiquimod." Journal of Leukocyte Biology, vol. 55, Feb. 1994, pp. 234-240.

Mark Marsh et al., "Endocytosis in Viral Replication," Traffic 2000 1: pp. 525-532.

Bart L. Haagmans et al., "Pegylated Interferon-a. Protects Type 1 Pneumocytes Against SARS Coronavirus Infection in Macaques," Nature Medicine, vol. 10, No. 3, Mar. 2004 pp. 290-293.

Sabine Mihm et al., "Interferon Type I Gene Expression in Chronic Hepatitis C," Laboratory Investigation (2004) 84, pp. 1148-1159.

Ron A.M. Fouchier et al., "Detection of Influenza A Viruses from Different Species by PCR Amplification of Conserved Sequences in the Matrix Gene," Journal of Clinical Microbiology, vol. 38, No. 11, Nov. 2000, pp. 4096-4101.

Louis DeTulleo et al., "The Clathrin Endocytic Pathway in Viral Infection," The EMBO Journal, vol. 17, No. 16, 1998, pp. 4585-4593.

Sara Cherry et al., "Entry is a Rate-Limiting Step for Viral Infection in a *Drosophila melanogaster* Model of Pathogenesis," Nature Immunology, vol. 5, No. 1, Jan. 2004, pp. 81-87.

Timothy W. Schacker et al., "Imiquimod 5% Cream Does Not Alter the Natural History of Recurrent Herepes Genitalis: a Phase II, Randomized, Double-Blind, Placebo-Controlled Study", Antimicrobial Agents and Chemotherapy, vol. 46, No. 10, Oct. 2002, pp. 3243-3248.

David I. Bernstein et al., "Evaluation of Imiquimod 5% Cream to Modify the Natural History of Herpes Labialis: A Pilot Study," Clinical Infectious Diseases, 2005:41, pp. 808-814.

PCT International Search Report and Written Opinion dated May 21, 2008 for PCT/US06/14803.

Office Action dated Jun. 20, 2007 for U.S. Appl. No. 10/751,371.

Office Action dated Aug. 19, 2008 for U.S. Appl. No. 11/318,659.

Office Action dated Sep. 16, 2008 for U.S. Appl. No. 11/109,553.

* cited by examiner

Imiquimod (R-837)    Resiquimod (R-848)

SEQUENCE LISTING

<160> NUMBER OF SEQ ID NOS: 4

<210> SEQ ID NO 1
<211> LENGTH: 27
<212> TYPE: DNA
<213> ORGANISM: indian macaca mulata
<220> FEATURE:
<221> NAME/KEY: mRNA
<222> LOCATION: (1)..(27)
<223> OTHER INFORMATION: y is a pyrimidine that can be either a "c" or "t" w is a weak base that can be either an "a" or "t"
<300> PUBLICATION INFORMATION:
<301> AUTHORS: Sanda Clejan, E. Mandrea, Ivona V. Pandrea, J. Dufour,
      S. Japa, R.S. Veazey
<302> TITLE: Immune responses induced by intranasal imiquimod and
      implications for therapeutics in rhinovirus infections
<303> JOURNAL: J. Cell. Mol. Med
<304> VOLUME: 9
<305> ISSUE: 2
<306> PAGES: 457-461
<307> DATE: 2005-02-27
<308> DATABASE ACCESSION NUMBER: 2209 P 005
<309> DATABASE ENTRY DATE: 2006-04-12
<313> RELEVANT RESIDUES IN SEQ ID NO: (1)..(27)

<400> SEQUENCE: 1
gaagcttyct cctgyytgaw ggacaga                                           27

<210> SEQ ID NO 2
<211> LENGTH: 29
<212> TYPE: DNA
<213> ORGANISM: indian macaca mulata
<220> FEATURE:
<221> NAME/KEY: mRNA
<222> LOCATION: (1)..(29)
<223> OTHER INFORMATION: n is an unknown which can be an "a", "c", "t",
      or "g"
<220> FEATURE:
<221> NAME/KEY: misc_feature
<222> LOCATION: (24)..(24)
<223> OTHER INFORMATION: n is a, c, g, or t
<300> PUBLICATION INFORMATION:
<301> AUTHORS: Sanda Clejan, E. Mandrea, Ivona V. Pandrea, J. Dufour,
      S. Japa, R.S. Veazey
<302> TITLE: Immune responses induced by intranasal imiquimod and
      implications for therapeutics in rhinovirus infections
<303> JOURNAL: J. Cell. Mol. Med.
<304> VOLUME: 9
<305> ISSUE: 2
<306> PAGES: 457-461
<307> DATE: 2005-02-27
<308> DATABASE ACCESSION NUMBER: 2209 P 005
<309> DATABASE ENTRY DATE: 2006-04-12
<313> RELEVANT RESIDUES IN SEQ ID NO: (1)..(29)

<400> SEQUENCE: 2
ggggatcctc tgacaacctc ccangcaca                                         29

<210> SEQ ID NO 3
<211> LENGTH: 21
<212> TYPE: DNA
<213> ORGANISM: indian macaca mulata
<220> FEATURE:
<221> NAME/KEY: mRNA
<222> LOCATION: (1)..(21)
<300> PUBLICATION INFORMATION:
<301> AUTHORS: Sanda Clejan, E. Mandrea, Ivona V. Pandrea, J. Dufour,
      S. Japa, R.S. Veazey
<302> TITLE: Immune responses induced by intranasal imiquimod and
      implications for therapeutics in rhinovirus infections
<303> JOURNAL: J. Cell. Mol. Med.
<304> VOLUME: 9
<305> ISSUE: 2
<306> PAGES: 457-461
<307> DATE: 2005-02-27
<308> DATABASE ACCESSION NUMBER: 2209 P 005
<309> DATABASE ENTRY DATE: 2006-04-12
<313> RELEVANT RESIDUES IN SEQ ID NO: (1)..(21)

<400> SEQUENCE: 3
cttgaatgtg ctgatgacag g                                                 21

<210> SEQ ID NO 4

-continued

```
<211> LENGTH: 22
<212> TYPE: DNA
<213> ORGANISM: indian macaca mulata
<220> FEATURE:
<221> NAME/KEY: mRNA
<222> LOCATION: (1)..(22)
<300> PUBLICATION INFORMATION:
<301> AUTHORS: Sanda Clejan, E. Mandrea, Ivona V. Pandrea, J. Dufour,
       S. Japa, R.S. Veazey
<302> TITLE: Immune responses induced by intranasal imiquimod and
       implications for therapeutics in rhinovirus infections
<303> JOURNAL: J. Cell. Mol. Med.
<304> VOLUME: 9
<305> ISSUE: 2
<306> PAGES: 457-461
<307> DATE: 2005-02-27
<308> DATABASE ACCESSION NUMBER: 2209 P 005
<309> DATABASE ENTRY DATE: 2006-04-12
<313> RELEVANT RESIDUES IN SEQ ID NO: (1)..(22)

<400> SEQUENCE: 4
gcaagtgagc aggcatctca tc                                              22
```

METHOD OF TREATING GENITAL HERPES

CROSS-REFERENCE TO RELATED APPLICATIONS

This application is a continuation-in-part of U.S. application Ser. No. 11/318,659, filed Dec. 21, 2005, which is a continuation-in-part of U.S. application Ser. No. 11/109,553, filed Apr. 19, 2005, which is a continuation-in-part of U.S. application Ser. No. 10/751,371, filed Jan. 5, 2004, which claims priority from U.S. Provisional Application No. 60/438,431, filed Jan. 6, 2003.

TECHNICAL FIELD

The present invention generally relates to methods of stimulating an immune response in certain individuals. Methods to stimulate a host immune system against viral infections associated with common colds are disclosed. Methods to stimulate immune response of a virally infected individual through an immunomodifier such as a non-nucleoside imidazoquinolinamine (heterocyclic amine) are disclosed. Methods to stimulate immune response of an individual infected with influenza are also disclosed. Methods to stimulate immune response of individuals having various cancers, such as lung cancer, bronchogenic carcinoma, bronchoalveolar carcinoma and nasal type natural killer T cell lymphoma are disclosed. Methods to stimulate immune response of individuals having herpes simplex virus type 2 ("HSV-2"), the most common cause of recurrent genital herpes are disclosed.

BACKGROUND OF THE INVENTION

Uncomplicated cases of viral infections usually produce mild symptoms such as nasal discharge, obstruction of nasal breathing, swelling of the sinus membranes, sneezing, sore throat, cough, and headache. These symptoms generally last between one and two weeks. A mild infection is generally associated with the rhinoviruses and the coronaviruses. The uncomplicated infection is most often referred to as the "common cold."

At present, only symptomatic treatment is available for uncomplicated viral infections, "common colds." The treatments include the use of over-the-counter decongestants, cough suppressants, cough expectorants, aspirin, and acetaminophen. The treatments, however, do not cure or even shorten the duration of the illness. Moreover, many of the treatments have side effects such as drowsiness, dizziness, insomnia, or upset stomach. Because of the diversity of the viruses, vaccines may not be effective in preventing the onset of colds.

It has been estimated that in the course of a year, individuals in the United States suffer one billion colds. Colds thus have a tremendous societal cost in lost work days and lost school days. People suffer symptomatic discomfort. Even people receiving symptomatic treatment still suffer from some discomfort and additionally suffer side effects of treatment. Moreover, influenza affects many people, typically causing more serious symptoms than a cold.

Aldara™ (imiquimod; manufactured by 3M Corporation, St. Paul, Minn.) cream, is a prescribed patient-applied topical cream for treating external genital and perianal warts. The Aldara™ product label does not recommend using it for any other purposes.

Genital herpes is a significant health problem worldwide and continues to increase in prevalence in the United States. In individuals in the United States over 12 years old, HSV-2 seroprevalence has increased from 16.4% in 1976 to 21.8% in 1994 and is still rising. Thus, the current incidence of genital herpes caused by HSV-2 in the United States is roughly one in four or five adults, with approximately 50 million people infected with genital herpes and an estimated 0.5 million new genital herpes infections occurring each year.

HSV-2 causes periods of active disease—presenting as painful blisters containing infectious virus particles—that last 2-21 days and are followed by remission when the sores disappear. Most cases of genital herpes are asymptomatic, although viral shedding may still occur. HSV-2 is transmitted by direct contact with a sore or body fluid of an infected individual. After initial infection, the virus moves to sensory nerves, where it resides as a life-long, latent virus. The virus lies dormant in lumbrosacral that supply sensation to the genitals, perineum and upper legs.

Occasionally, these viruses reactivate and return to the area of skin infected during the primary infection. Intermittent reactivation of viral replication can result in both symptomatic and subclinical recurrences because HSV-2 can reside latently in the sensory ganglion. The reactivation rate is highly variable and very difficult to predict from individual to individual. Many believe cell-mediated immunity plays a major role in restricting reactivation yet this role is not currently well understood.

Treatments are available to reduce the symptoms and speed up the healing process of herpes infections but there is currently no cure. Antiviral drugs, such as aciclovir and valaciclovir, taken orally, reduce viral reproduction and shedding, and some topical creams, such as Docosanol and Tromantadine prevent the virus from entering the skin. Some other drugs reduce herpetic symptoms by synergising with oral antiviral medication. Cimetidine and probenecid can reduce aciclovir clearance and aspirin can reduce inflammation associated with viral infection.

While the above listed treatment methods are effective, they require constant daily dosing of medications which can be expensive. Additionally, once discontinued, the medications have no posttreatment effect and the patient immediately reverts back to pre-treatment reactivation levels. Therefore, it would be advantageous to develop a treatment for HSV-2 that would be effective in treating viral outbreaks when they occur and would reduce the rate of outbreak recurrences after the treatment is discontinued.

In 2002, Timothy W. Schacker et al. hypothesized that long term HSV-2 treatment could be achieved through enhancing the host's ability to control the virus and that topical application of imiquimod in the form of Aldara™ to herpes lesions could achieve this result. Timothy W. Schacker et al., *Imiquimod 5-Percent Cream Does Not Alter the Natural History of Recurrent Herpes Genitalis: a Phase II, Randomized, Double-Blind, Placebo-Controlled Study*, Antimicrobial Agents and Chemotherapy, October 2002, pp. 3243-48. Schacker et al.'s hypothesis was based on the knowledge that imiquimod produces a localized immunological response in the area of skin to which it is applied as explained above and successful results in studies where imiquimod was applied to herpes lesions in Guinea Pigs. To test their hypothesis, Schacker et al. performed a phase II, randomized, double-blind, placebo-controlled study on 235 human patients. The results of the study showed that there was no statistically significant difference in outbreak recurrence times between those patients treated with imiquimod and those treated with placebo. Therefore, Schacker et al. concluded that imiquimod was not effective in reducing the rate of herpes outbreaks in humans.

SUMMARY OF THE INVENTION

Methods to reduce the duration of symptoms associated with the common cold, viral rhinitis or influenza, without producing any substantial side effects generally associated with symptomatic treatment are disclosed. To reduce the duration of symptoms associated with the common cold or influenza, methods relate to applying an imidazoquinolinamine formulation, such as, for example, an imiquimod salve within a person's nostrils, also referred to as nares. Any suitable imidazoquinolinamine formulation can be used to reduce the duration of symptoms associated with the common cold, viral rhinitis or influenza. Further, in another embodiment, the method can be used to treat various cancers including lung cancer, bronchogenic carcinoma, bronchoalveolar carcinoma and nasal type natural killer T cell lymphoma.

Application of imiquimod to the inside of the nostrils and in particular to the mucosal membrane of an infected individual stimulates host cells to secrete chemical substances such as interleukins and interferons that promote the individual's immune response.

A method to reduce the duration of symptoms associated with the common cold or viral rhinitis includes application of ½ packet of Aldara™ (imiquimod formulation; 0.25 g of 5% active ingredient) into both nostrils (nares) every 12 hours for a total of 4 applications. The formulation may be applied by way of an applicator or any other suitable means. The formulation is applied into both nares at the onset of the cold. The onset is the day when the first cold symptoms appear. If the formulation is not applied on the first day the symptoms appear, it should be applied by the next day. The formulation is applied twice daily for two consecutive days. The formulation can be massaged into the internal surface of each naris. The treatment of the second naris is after the treatment of the person's first naris.

An imiquimod formulation is applied as described above at the onset of first cold symptoms such as nasal irritation, watery eyes, nasal drip or other early cold symptoms. The earlier the imiquimod formulation is applied after the onset of the cold, the shorter the recovery from the cold. An imiquimod formulation may also be applied the next day after the onset of the cold.

A method to reduce the duration of symptoms associated with the common cold or viral rhinitis includes application of a coating of the mucosal membrane within each naris with Neosynepherine® (phenylephrine) prior to applying the Aldara™ formulation within each naris. The Neosynepherine® (phenylephrine) may be applied in the form of an over-the-counter liquid formulation by means of a spray bottle. The Neosynepherine® (phenylephrine) is preferably applied 15 minutes before applying the imiquimod formulation.

Another aspect of the present invention is directed to a method of increasing the time period between outbreaks of genital herpes comprising providing an imidazoquinolinamine formulation, disposing an amount of the imidazoquinolinamine formulation into a first nare of an individual infected with Herpes Simplex Virus type 2, covering at least a portion of the internal surface of the individual's first nare with a portion of the amount of the imidazoquinolinamine in the nare, massaging the portion of the amount of the imidazoquinolinamine into the internal surface of the first nare, disposing the amount of the imidazoquinolinamine formulation into a second nare of the individual, covering at least a portion of the internal surface of the second nare with a portion of the amount of the imidazoquinolinamine in said nare and massaging the portion of the amount of the imidazoquinolinamine into the internal surface of said nare. The imidazoquinolinamine formulation is first applied within 12 hours after an appearance of first symptoms and is reapplied every 12 hours thereafter until it has been applied four times to each nare.

Other novel features, characteristics and aspects of the methods described herein can be further understood with reference to the below described drawings, detailed description, examples, and the appended claims.

BRIEF DESCRIPTION OF THE DRAWINGS

The drawings are provided to illustrate some of the embodiments of the disclosure. It is envisioned that alternate configurations of the embodiments of the present disclosure maybe adopted without deviating from the disclosure as illustrated in these drawings.

DETAILED DESCRIPTION

While the concepts of the present disclosure are illustrated and described in detail in the drawings and the description below, such an illustration and description is to be considered as exemplary and not restrictive in character, it being understood that only the illustrative embodiment is shown and described and that all changes and modifications that come within the spirit of the disclosure are desired to be protected.

Figure 1:
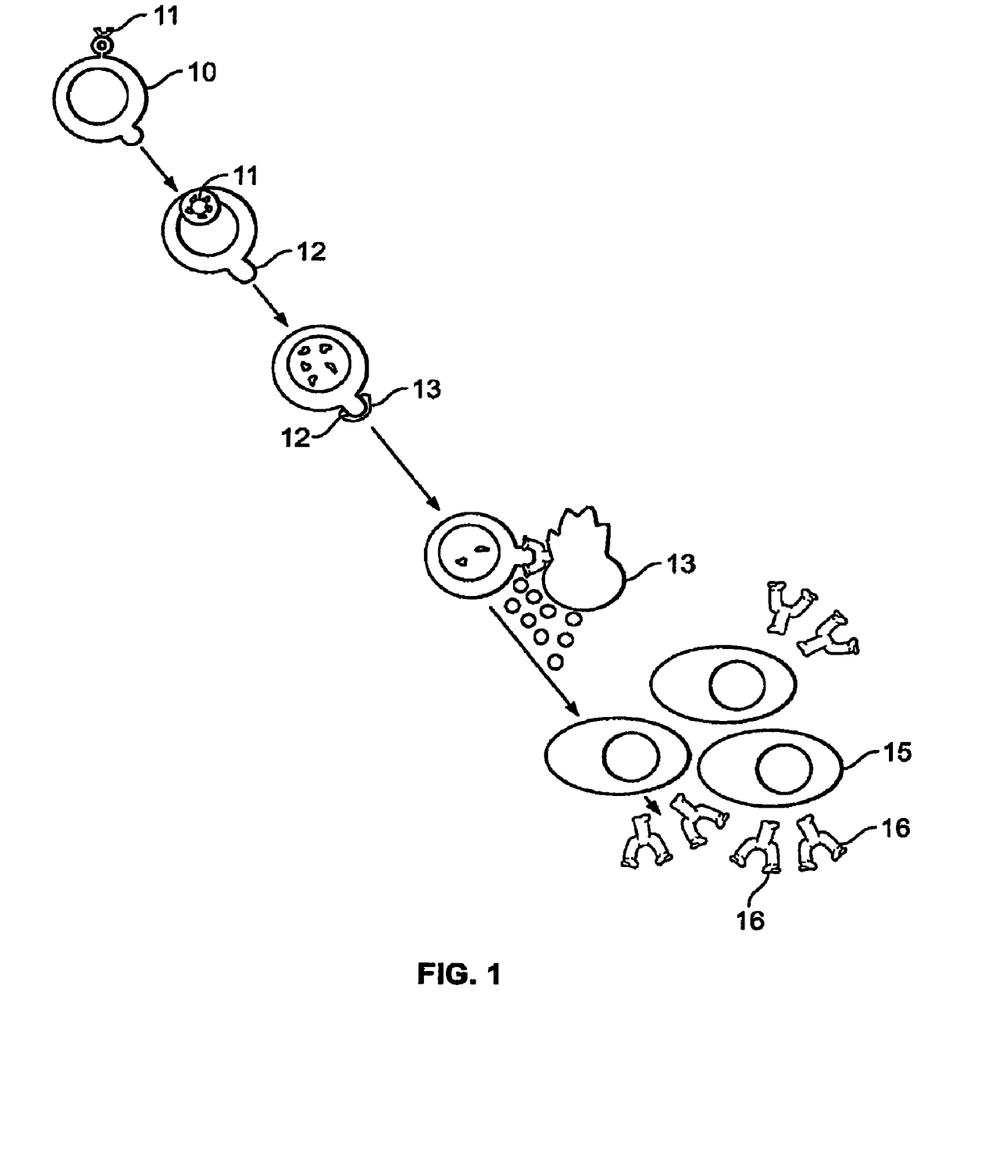
FIG. 1 pictorially illustrates how cytokines promote and regulate the immune cell response.

FIG. 1 generally describes how some cells in the human body operate as part of the host immune system to combat infection. In FIG. 1, a lymphocyte (monocytic dendritic cell) 10 takes in an antigen 11 and displays part of the digested antigen 13 with a marker molecule 12 to a mature T cell 13.

The T cell secretes cytokines 14 which help stimulate the B cell to mature into a plasma cell 15 which produces antibodies 16. The foreign antigen in the present diagram is viral. This is known as T-helper 2 mode.

Figure 2:
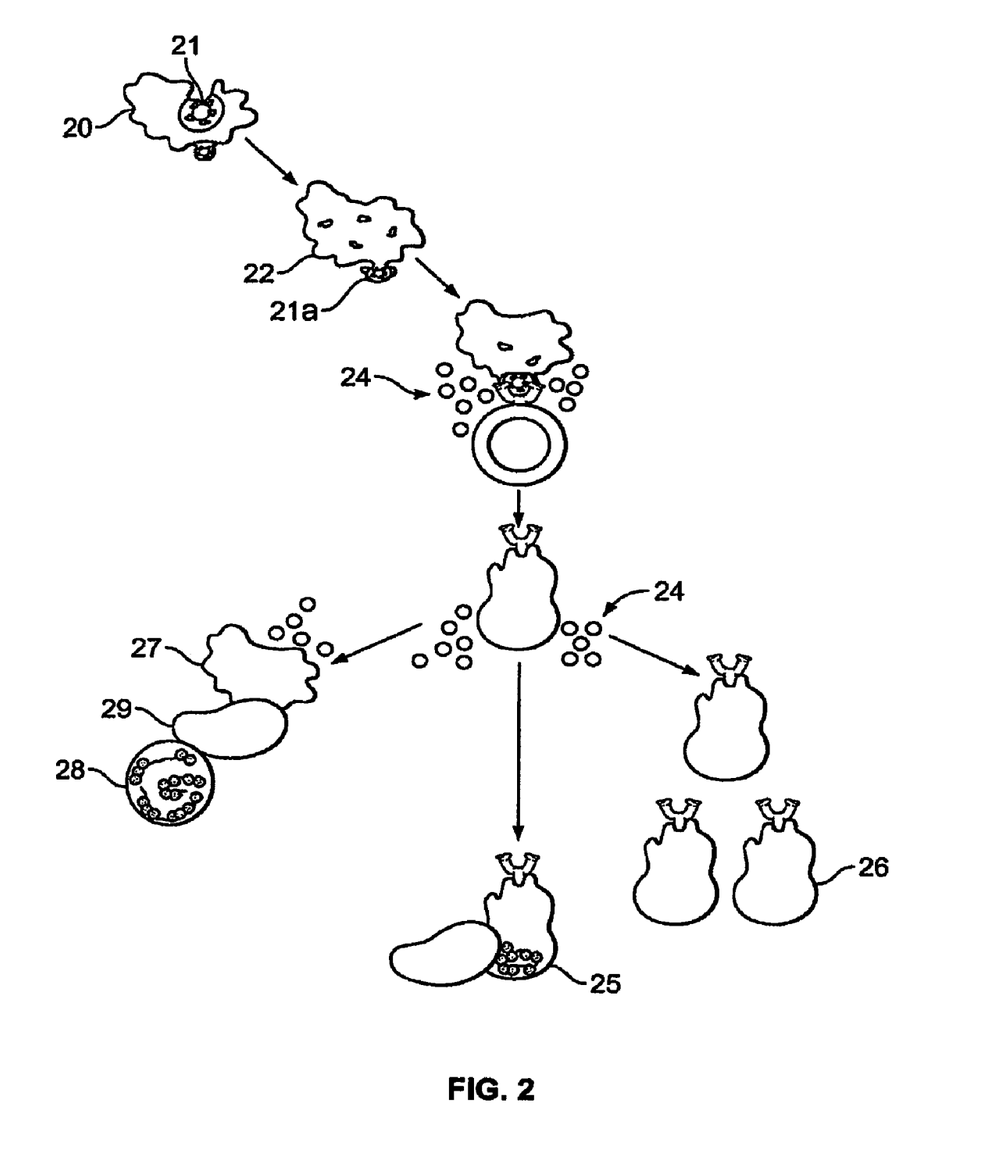
FIG. 2 pictorially illustrates further how cytokines help to regulate and promote the body's immune response.

This figure is a schematic representation of the adapted immune system which works much more slowly than the innate immune system. As part of the innate immune system, the skin and mucous membranes have been shown to be able to produce and secrete cytokines such as TNF-a, and the like. FIG. 2 discloses a macrophage 20 digesting a foreign antigen 21. The macrophage 20 displays antigen fragments 21a on its marker 22 to an immature T cell 23. Cytokines 24 are produced and help the T cell mature. Further cytokines 24 actually produced by the maturing T cell help the maturing T cell evolve into killer cells 25 and helper T cells 26. Cytokines 24 also help attract additional macrophages 27, granulocytes 28, and other lymphocytes to the area of infection thereby promoting an attack on infected cells 29 (this is now known as T-helper 1 mode).

Imiquimod enhances both the innate and adapted cell-mediated immune pathways to stimulate the production of various cytokines. For example, imiquimod stimulates the innate immune response by inducing the synthesis and release of cytokines, including IFN-a and TNF-a in both humans and animal studies. Inhalation of imiquimod results in even larger amounts of IFN-a and TNF-a, to the point of creating flu-like symptoms. Production of various cytokines by the activated innate immune system results in the strengthening of the cell-cell interaction. For example, monocytes, macrophages, B cells, and dendritic cells (including Langerhan cells; LC) are targeted by imiquimod.

Figure 4:
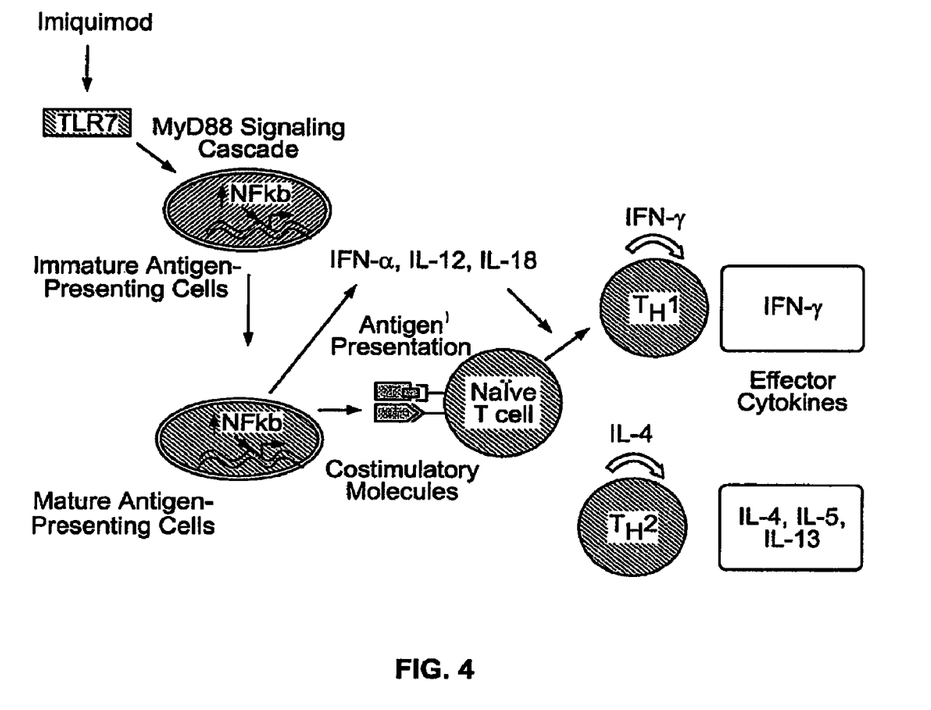
FIG. 4 pictorially illustrates a possible mode of action of an imidazoquinolinamine such as imiquimod in stimulating host immune system.

A proposed mechanism by which imiquimod may activate the above-mentioned target cells is via the activation of Toll-like receptors (TLRs), a family of pathogen recognition receptors located on the cell surface of various innate immune cells such as dendritic cells. Activation of TLRs, such as, for example, TLR7 results in the downstream activation of a signal cascade mediated by MyD88 and various effector cytokines such as IFN-a, IL-12, and IL-18 are produced (FIG. 4).

A proposed mechanism of action for imiquimod to activate the cell-mediated immune response is through an indirect stimulation of T cells by producing Th-1 cytokine IFN-y. Imiquimod also enhances the migration of LCs to the regional lymph nodes to enhance antigen presentation to T cells. In vitro assays have established that exposure of LCs to imiquimod results in increased gene expression for TF-a, IL-1β, and IL-12, and also secretion of IFN-γ by imiquimod-treated T cells compared to untreated cells.

Studies have shown that immune response modifiers such as imiquimod and resiquimod are TLR7 agonists and induce type 1 interferon in numerous species including humans. Imiquimod and resiquimod induce IFN-a from purified plasmacytoid dendritic cells.

Thus imiquimod and resiquimod stimulate the local production of various cytokines such as IL-12, IL-18, IL-1β, IFN-a, and IFN-γ to promote both innate as well as cell-mediated immunity.

The common cold causes a group of symptoms that usually are easily recognized by patients and doctors. About 50 percent of patients will develop a sore throat, which is often the first symptom to appear since it can occur as early as 10 hours after infection. This is followed rapidly by the most common symptoms of the common cold—congested nasal and sinus passages, a runny nose and sneezing. Hoarseness and cough are less likely to occur, but they may last longer than other symptoms, sometimes for several weeks.

Most patients diagnose the common cold by the typical symptoms of runny nose, congestion and sneezing, and rarely consult medical attention. Symptoms typically peak on the second, third or fourth days of infection and last about one week to 10 days. Up to 25 percent of people may have persistent symptoms, such as a nagging cough that can last for several weeks.

The methods disclosed herein stimulate the immune system response as described in FIGS. 1, 2, and 4. The methods disclosed herein promote host cells to secrete chemicals and cytokines such as interferons and interleukins, which impact the host cellular immune response at least partially as shown in FIGS. 1, 2, and 4.

Figure 5:
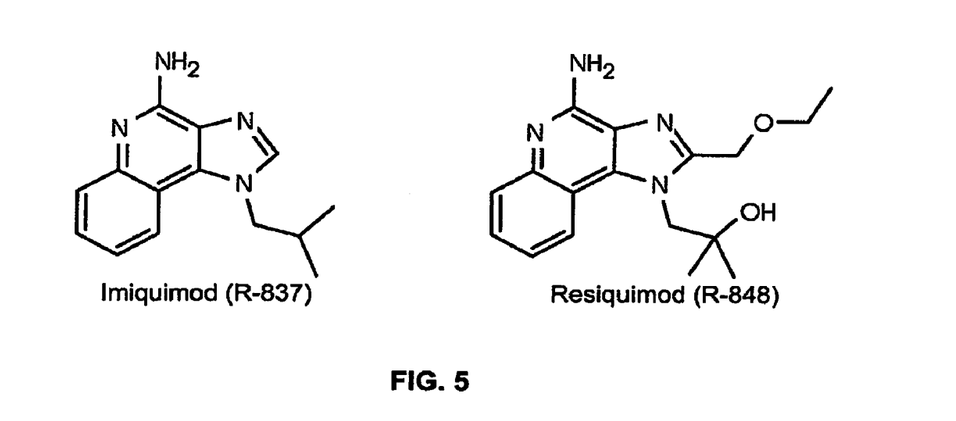
FIG. 5 shows the structural formulae for imiquimod and resiquimod.

Low molecular weight heterocyclic non-nucleoside imidazoquinolinamines can be used to treat viral rhinitis. One such imidazoquinolinamine is imiquimod whose IUPAC nomenclature is (1-(2-methylpropyl)-1H-imidazo)[4,5-c]quinolin-2-amine. Imiquimod may also be referred to as R-837. Another imidazoquinolinamine is resiquimod, whose IUPAC nomenclature is 4-amino-2-ethoxymethyl-a,a-dimethyl-1H-imidazol [4,5-c]quinoline-lethanol. Resiquimod may also be referred to as R-848. (see FIG. 5).

To provide effective treatment, a formulation of imiquimod commonly used to treat warts can be used. For example, the formulation sold in salve format under the brand name Aldara™ is effective. It is believed that other imiquimod formulations such as imiquimod in a fluid formulation or in a fine powder formulation might be effective.

A method to reduce the duration of symptoms associated with the common cold or viral rhinitis includes application of ½ packet of Aldara™ (imiquimod formulation; 0.25 g of 5% active ingredient) into both nostrils (nares) every 12 hours for a total of 4 applications. Each gram of 5% Aldara™ cream contains 50 mg of imiquimod as active ingredient.

In an embodiment, an applicator is used to disperse the imiquimod within each naris. The applicator used can be a cotton swab. See FIG. 3a. The swab should be of suitable size to fit internally within each naris such that the exterior of the swab can move freely within each naris and make substantial contact with the naris' mucosal membrane. In an embodiment, the imiquimod salve is combined with the swab shown in FIG. 3a by applying a 4 mm$^3$ dab of the imiquimod salve on the head of the swab. The swab is then inserted in a naris and moved around within the naris so as to spread the salve over the naris' mucosal membrane.

In another embodiment, the foregoing methods utilizing imiquimod may also be used to treat influenza. The applicator is used to disperse the imiquimod within each naris. The applicator used can be a cotton swab. See FIG. 3a. The swab should be of suitable size to fit internally within each naris such that the exterior of the swab can move freely within each naris and make substantial contact with the naris' mucosal membrane. In an embodiment, the imiquimod salve is combined with the swab shown in FIG. 3a by applying a 4 mm$^3$ dab of the imiquimod salve on the head of the swab. The swab is then inserted in a naris and moved around within the naris so as to spread the salve over the naris' mucosal membrane. For treating influenza, the imiquimod may be applied once a day for two days. The nares are then squeezed against the septum to improve absorption.

In a further embodiment, the foregoing methods utilizing imiquimod may also be used to treat various cancers such as lung cancer, bronchogenic carcinoma, bronchoalveolar carcinoma and nasal type natural killer T cell lymphoma. The applicator is used to disperse the imiquimod within each naris. The applicator used can be a cotton swab. See FIG. 3a. The swab should be of suitable size to fit internally within each naris such that the exterior of the swab can move freely within each naris and make substantial contact with the naris' mucosal membrane. In an embodiment, the imiquimod salve is combined with the swab shown in FIG. 3a by applying a 4 mm³ dab of the imiquimod salve on the head of the swab. The swab is then inserted in a naris and moved around within the naris so as to spread the salve over the naris' mucosal membrane. The nares are then squeezed against the septum to improve absorption.

Figures 3A, 3B, 3C, 3D:
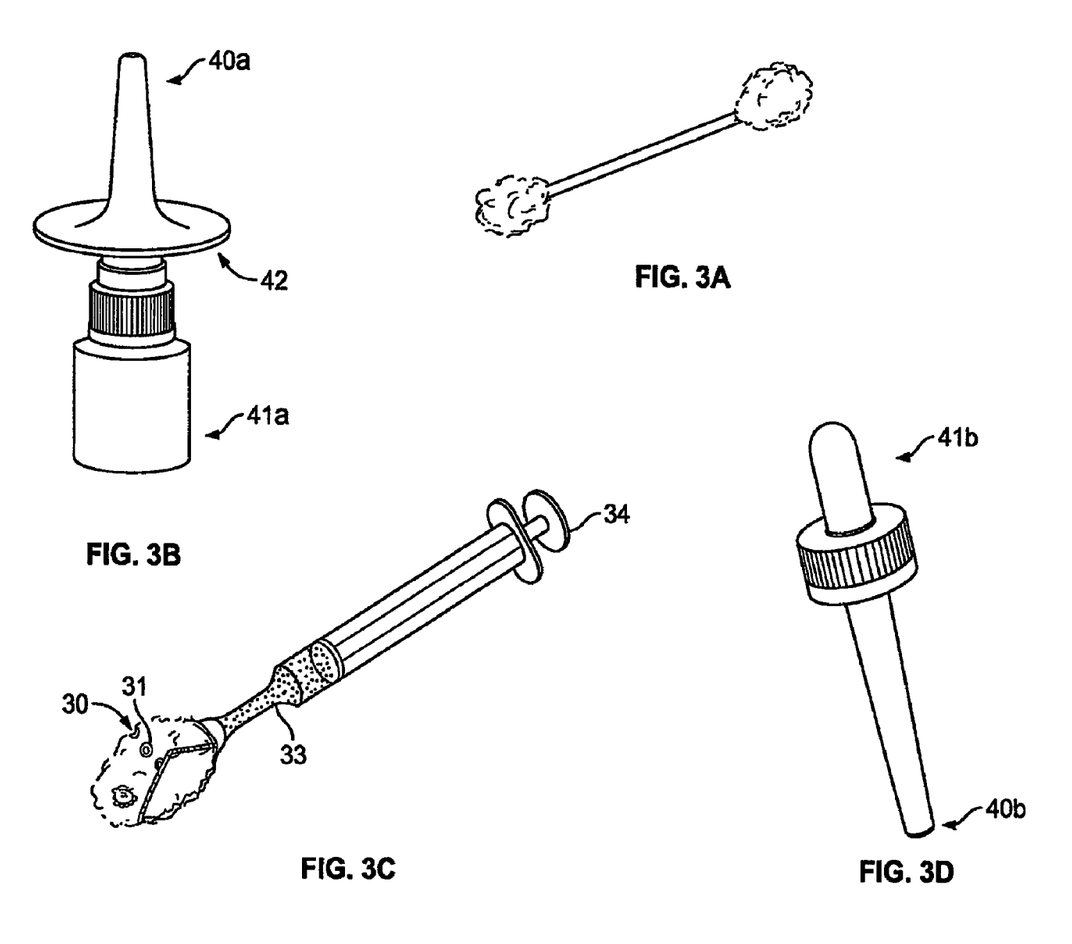
FIG. 3a shows a side and top perspective view of a swab-type applicator for use with an imiquimod formulation
FIG. 3b shows a side and top perspective view of a spray nozzle coupled to a bottle; the spray nozzle is the applicator for a liquid imiquimod formulation.
FIG. 3c shows a cross-sectional side view of an injection tube interfaced with a hollow swab head which can be used to apply an imiquimod formulation; the injection tube is connected to a vessel and the vessel has a piston actuator to inject a certain amount of imiquimod through the swab head into a naris.
FIG. 3d shows a side and perspective view of a dropper-type nozzle which dispenses liquid imiquimod in droplet form; the nozzle is connected to a squeeze bulb.

The swab shown in FIG. 3a is not the only type of applicator which can be used to apply an amount of imiquimod salve to a naris. Many other types of applicators can be used. For instance, an applicator with a hollow swab head fluidly connected with an injection tube would work. See FIG. 3c. The hollow swab head 30 would have a series of tiny apertures 31 through which the salve could be extruded. Extrusion through the tiny holes would occur by way of actuating an amount of salve in the injection tube 33 to flow into the hollow swab head 30. Actuation could occur by a plunger 34. Once the salve is extruded, the hollow swab head is moved around within the naris so as to spread the salve within the naris. The swab head could have many configurations. Additionally, it is feasible that one could use an injection tube alone to dispense the salve in the naris. The salve could then be spread by a cotton swab, a finger or some other means.

Instead of using imiquimod in a salve formulation, one may also use imiquimod in a liquid formulation. If an imiquimod liquid formulation is used, the applicator can be a spray nozzle 40a, FIG. 3b, or a dropper nozzle 40b, FIG. 3d. The nozzles 40a, 40b could be interfaced to vessels such as bottles 41a or squeeze bulbs 41b. The vessels 41a, 41b and nozzles 40a and 40b would be configured so that a predetermined actuation sequence would emit an effective dosage of imiquimod from the nozzle into the naris. For instance, to emit imiquimod from the spray nozzle 40a, an operator would simply depress pump 42 interfaced with the spray nozzle. In addition to the above, the applicator could simply be a finger or any other member which would fit within a naris and allow dispersion of the imiquimod formulation within the naris.

It is preferable after first applying the imiquimod formulation to the internal surface of a naris or nares, i.e., within the naris, to massage the formulation into the naris' mucosal membrane.

Each of a person's two nares is treated in the same fashion. Treatment of the second naris is immediately after the first naris. Massaging of the salve into at least a portion of the internal surface of each naris can occur after the salve has been applied to both nares.

Prior to treating each naris with the imiquimod formulation, each naris can be precoated with Neo-Synephrine® (a solution of about 10% phenylephrine hydrochloride) at least 15 minutes before applying the imiquimod formulation. Prepping the nares with the formulation facilitates prolonged contact of the imiquimod to the nares' internal surfaces by helping to prevent wash-off due to nasal secretion. Phenylephrine is a decongestant that works by constricting (shrinking) blood vessels (veins and arteries). Constriction of blood vessels in the sinuses, nose, and chest allows drainage of these areas, which decreases congestion. Any other suitable alpha-adrenergics or other decongestants may also be used.

The utility of the above-described method for treating persons with viral infections can also be seen by reference to the below in vivo experiments.

In each of the tests, an imiquimod salve was used. The formulation was that commonly used to treat warts and sold under the brand name Aldara™. The salve was applied to each naris of the test subject by use of a common cotton swab. Either a 4 mm³ dab of salve or ½ pack of 5% Aldara™ was placed on the swab head. The swab head was inserted into a naris. The swab was moved around inside the naris to distribute the salve over the mucosal membrane of the naris. Immediately, after application of the Aldara™ to the subject's first naris, a swab was used to apply the Aldara™ to the subject's second naris. Immediately after application to each naris, the salve was massaged into the mucosal membrane of each naris.

Application of an immunomodifier such as imiquimod to the internal surface of the nostrils stimulates innate immunity locally and thus helps to shorten the duration of cold symptoms.

EXAMPLES

Example 1

Alleviation of Viral Rhinitis Symptoms by Administering Imiquimod at or about the Onset of the Cold Symptoms A test sample of six patients was treated for viral rhinitis using imiquimod (5% topical cream Aldara™, manufactured by 3M Corporation, St. Paul, Minn.). The patients were diagnosed with viral rhinitis due to initial symptoms such as congested nasal passages (rhinitis), nasal drip or rhinorrhea, and sneezing. Contents from ½ packet of a standard imiquimod formulation such as, for example, Aldara™ were applied with a cotton swab into both nares by massaging gently but thoroughly. Approximately the contents from ½ packet of 5% Aldara™ was applied thoroughly along the inside surface of both nares. Initial application of Aldara™ to all the six patients occurred within 24 hours after the appearance of first symptoms resembling viral rhinitis, in order to maximize the efficiency of imiquimod in stimulating the immune system when the viral load is presumably smaller. The procedure was repeated every 12 hours for up to 48 hours. The imiquimod packets were refrigerated after opening, and the remaining contents were used for subsequent applications.

The patients were monitored for changes in the viral rhinitis symptoms. No untoward side effects were reported by any of the patients throughout the course of the treatment. The first sign of relief (reduced nasal congestion, nasal drip) was obtained between 12 and 36 hours after beginning the imiquimod treatment. Complete disappearance of symptoms (nasal congestion, sore throat, headache; malaise) was obtained within 48 hours of treatment. One patient with ulcerative colitis (a possible Th2-type disorder) did not suffer any further aggravation during the treatment. In an unrelated incident, during the course of treatment, one patient inhaled imiquimod and developed severe flu-like symptoms that spontaneously subsided within 24 hours. Therefore, care should be taken not to inhale the imiquimod formulation during application in the nostrils.

The results demonstrate that an imiquimod formulation is effective in reducing the duration of symptoms during viral rhinitis or common cold (TABLE 1). The imiquimod and other related compounds such as resiquimod stimulate the immune cells both locally and also systemically to mount a defense response against the viruses. The cold symptoms subsided within 48 hours compared to about a week or 10 days for untreated viral rhinitis. Formulations of imidazoquinolinamines such as, for example, imiquimod or resiquimod can thus be effectively used to mitigate symptoms during viral rhinitis. Depending on the intensity of the viral rhinitis, an imiquimod or resiquimod formulation or the treatment plan can be modified. For example, instead of every 12 hours, the imiquimod formulation can be applied every 8 hours. In addition, appropriate modifications of the amount of imiquimod can also be undertaken. Furthermore, any suitable method of administration can be implemented, such as, for example, using a swab, or a drip applicator or as a nasal spray.

Example 2

Alleviation of Viral Rhinitis Symptoms by Administering Imiquimod after the Onset of the Cold Symptoms Infected Test Subject #1 developed a sore throat with tingling in larynx, pharynx and uvula. 12 hours later, Subject 1 also developed congestion of the nose. One day later, the subject's initial symptoms intensified, and the subject further developed systemic symptoms such as malaise and headache. More than twenty four hours after the initial viral rhinitis symptoms appeared, Aldara™ was applied in each nostril with a Q-tip swab.

A 4 mm$^3$ dab of salve was placed on the swab head. The swab head was inserted into a naris. The swab was moved around in the naris so as to distribute the salve over the mucosal membrane of the naris. Immediately, after application of the Aldara™ to the subject's first naris, a swab was used to apply the Aldara™ to the subject's second naris. Immediately after application to each naris, the salve was massaged into the mucosal membrane of each naris. The subject was also treated with 2 teaspoons of standard cough suppressant guaifenesin/dextromethorphan (Wal-Tussin). The next day, malaise and headache were more pronounced and Aldara™ was reapplied with Q-tip to each nostril as described above. Also, 2 teaspoons of guaifenesin/dextromethorphan was administered.

Two days after the first application of Aldara™, marked improvement of symptoms, including malaise and headache was observed. Three days after the first application of Aldara™, some cough and rhinorrhea persisted, and by 4-5 days, all of the cold symptoms subsided.

Infected Test Subject #2 developed common cold with rhinorrhea and nose congestion. Aldara™ was applied once to each nostril every day for 3 days. By day three, except for post nasal drip, other cold symptoms subsided.

It was noted the effectiveness of the treatment decreased markedly if the imiquimod formulation was applied more than 2 days after the onset of the cold symptoms. Compared to Example 1, the Aldara™ treatment described in Example 2 required longer duration for complete symptom relief (see TABLES 1 and 2). This may be due to factors such as (i) delayed application of Aldara™ after the onset of the first cold symptoms, and (ii) infrequent application (once a day compared to twice a day in Example 1). Therefore, immediate application of Aldara™ or any other imiquimod formulation after the onset of the cold symptoms may result in quicker relief of cold symptoms.

It was also noted by the inventor and the inventor's wife, empirically on themselves, that if treatment occurred within 12 hours of onset of symptoms, the infection was terminated overnight. It is believed treatment may need to occur within six hours of onset to terminate the infection. It was also noted that the application of Aldara™ for more than two days may result in severe irritation of the nasal mucosa, possibly mediated by TNF-a.

TABLE 1

Viral rhinitis and treatment data with imiquimod

| Patient | Symptoms | Day 0[a] | Day 1 | Day 2 |
|---|---|---|---|---|
| Patients 1-6 | Local Symptoms: sore throat; nasal congestion; rhinitis; rhinorrhea | Present | Substantial reduction | Complete reduction |
| | Systemic Symptoms: headache; cough; malaise | Present | Substantial reduction | Complete reduction |

[a]onset of first cold symptoms and first administration of Aldara ™. Thereafter, Aldara ™ was administered every 12 hours for 48 hours.

TABLE 2

Viral rhinitis and treatment data with imiquimod delayed administration of imiquimod after the first onset of cold symptoms.

| Patient | Symptoms | Day 0[a] | Day 1[b] | Day 2 | Day 3 | Day 4 |
|---|---|---|---|---|---|---|
| Test Subject 1[c] | Local: Symptoms: sore throat; nasal congestion; rhinitis; rhinorrhea | Present | Present | Substantial reduction | Only mild rhinorrhea | Complete reduction |
| | Systemic Symptoms: headache; cough; malaise | Present | Present | Slight reduction | Substantial reduction | Complete reduction |
| Test Subject 2[d] | Local Symptoms: sore throat; nasal congestion; rhinitis; rhinorrhea | Present | Substantial reduction | Only mild rhinorrhea | Complete reduction | |

TABLE 2-continued

Viral rhinitis and treatment data with imiquimod delayed administration of imiquimod after the first onset of cold symptoms.

| Patient | Symptoms | Day 0[a] | Day 1[b] | Day 2 | Day 3 | Day 4 |
|---|---|---|---|---|---|---|
| | Systemic Symptoms: headache; cough; malaise | Present | Slight reduction | Substantial reduction | Complete reduction | |

[a]onset of first cold symptoms.
[b]first administration of Aldara ™. Thereafter, Aldara ™ was administered every 24 hours up to 3 days.
[c]cough suppressant was also administered.
[d]Aldara ™ was administered on Day 0, when the cold symptoms first appeared. Thereafter, Aldara ™ was administered every 24 hours up to 3 days.

Example 3

Prolonged Remission Period Between Outbreaks of Genital Herpes by Administration of Imiquimod During Outbreaks A test sample of four patients was treated for HSV-2 using imiquimod (5% topical cream Aldara™, manufactured by 3M Corporation, St. Paul, Minn.). The patients were diagnosed with HSV-2 due to typical outbreak symptoms such as lesions. For each patient, contents from ½ packet of a standard imiquimod formulation such as, for example, Aldara™ were applied with a cotton swab into both nares by massaging gently but thoroughly. Thus, the contents were applied thoroughly along the inside surface of both nares. Initial application of Aldara™ to all the four patients occurred within 12 hours after the appearance of first symptoms resembling an outbreak of genital herpes. The application procedure was repeated every 12 hours up to 48 hours so that a total of four applications was administered to each patient. The imiquimod packets were refrigerated after opening, and the remaining contents were used for subsequent applications.

Prior to treatment with Aldara™, the four patients were having herpes outbreaks at fairly regular intervals. Patients 1, 2 and 3 were experiencing outbreaks every 2 to 3 months and Patient 4 was having outbreaks once a month. Each of the four patients then began treatment by undergoing the 48 hour Aldara™ regimen detailed above each time he or she experienced an outbreak. After undergoing 2 to 4 regimens, each patient experienced a prolonged period of remission before the next outbreak. Patient 1 did not have another outbreak for approximately 3.5 years, Patient 2 did not have another outbreak for approximately 6 months, Patient 3 did not have another outbreak for approximately 10 months and Patient 4 did not have another outbreak for approximately 2 months. See Table 3 below summarizing these results.

TABLE 3

Genital Herpes treatment data with imiquimod

| Patient | Pre-Treatment Remission Interval (Approximate) | Post-Treatment Remission Interval (Approximate) |
|---|---|---|
| Patient 1 | 2-3 months | 3.5 years |
| Patient 2 | 2-3 months | 6 months |
| Patient 3 | 2-3 months | 10 months |
| Patient 4 | 1 month | 2 months |

The results demonstrate that an imiquimod formulation is effective in reducing the frequency of genital herpes outbreaks and increasing the length of the intervening remission period between outbreaks. These results are unexpected and surprising in light of the teachings and conclusions of Schacker et al. who found imiquimod was ineffective in prolonging HSV-2 remission in humans. The discrepancy may be explained by noting that imiquimod and other related compounds such as resiquimod when used in conjunction with the present invention stimulate a systemic immunological response to mount a defense response against HSV-2. Imiquimod's ability to produce a localized immunological response has been long known and led to Schacker et al.'s hypothesis that applying it to herpes lesions would increase remission intervals. However, although unexpected, it appears HSV-2 can be controlled by generating a systemic immunological response as provided by the present invention.

The invention is further described with reference to the following assay demonstrating the effectiveness of imiquimod on Macaque monkeys. In the assay, messenger RNA levels of interferon (IFN)-a were quantified. Quantification demonstrated 2-5 fold increases in nasal secretions following a single nasal application of imiquimod as compared with untreated macaques. The assay also indicated a rapid induction of IFN-a 1-5 hours post treatment, and a proportional increase of tumor necrosis factor (TNF)-a which remained 3 times above the controls even at 6 h post nasal treatment. No adverse reactions to treatment were found in macaques when the cream was used during this short period of time. The assay demonstrates that nasal application of imiquimod rapidly induces high levels of IFN-a and TNF-a production and therefore may limit the acquisition of the virus.

Figure 6A:
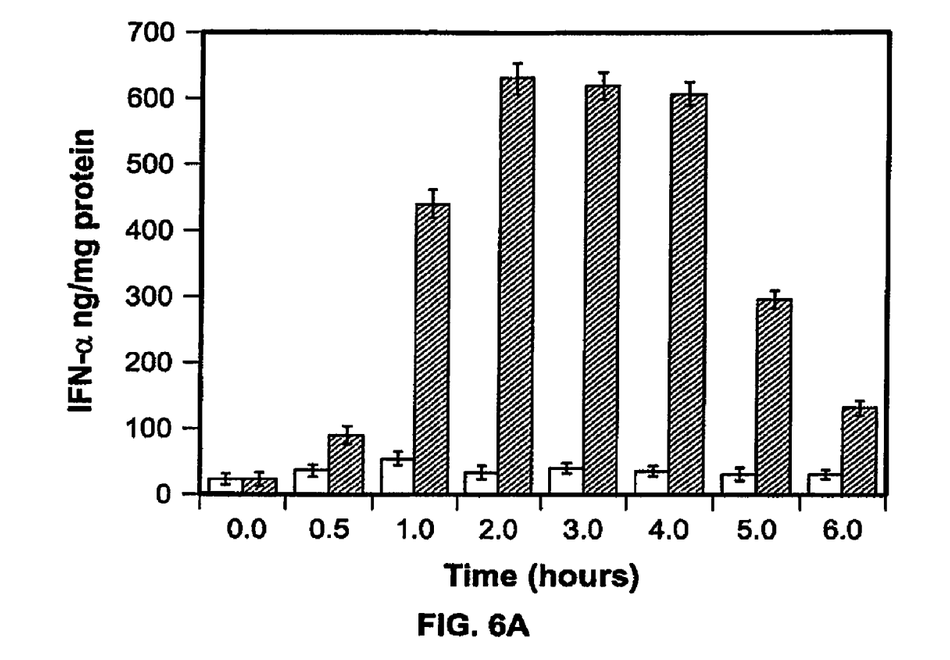
FIGS. 6A-6B show a time course of IFN-a (A) and TNF-a (B) induction following nasal application of imiquimod (n=5) ☐ or only base cream in controls (n=3) ☐.
Figure 6B:
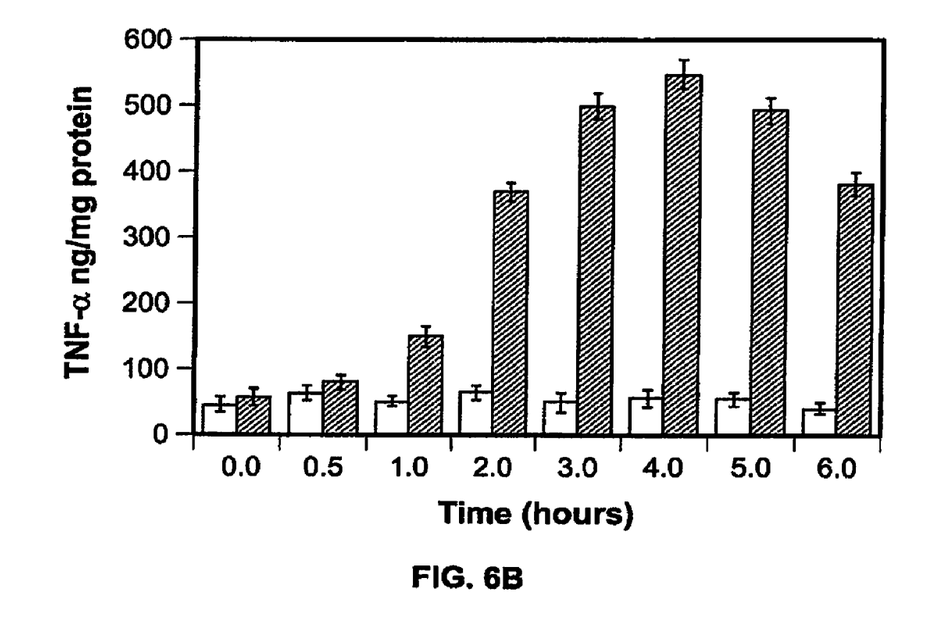

The assay was limited to examining nasal secretions following nasal application (both nares) of imiquimod, because it is believed that this is the entry site where an immune response will be first observed. The assay evaluated the appearance of mRNA IFN-α and TNF-a in Macaca mulatta macaques and compared it with a control group treated with a base cream (without imiquimod) or simply anesthetized for the same time interval as the treated group. ELISA measurements of IFN-a and TNF-a (FIGS. 6A-6B) showed a very significant increase ($p<0.0001$) over time of both cytokines (IFN-a to 630 ng/mg protein (FIG. 6A); TNF-a to 540 ng/mg protein (FIG. 6B) as compared with a minimal and steady concentration of IFN-a and TNF-a in the control group (FIGS. 6A-6B).

Kinetic studies of IFN-a and TNF-a levels showed a very rapid induction of IFN-a even at 1 h post treatment increasing to 5 times basal level at 3 h, remaining near maximal level at 4 h, but decreasing rapidly to near basal level at 6 h post treatment. TNF-a also increased proportionally, but slightly less than IFN-a peaking at 4 h, but remaining high even at 6 h post treatment. The significance of the data is two-fold. First, intranasal administration of imiquimod cream (5%) produced enough IFN-a in a short period of time, so the cream can be applied daily in order to have 5-6 h of good efficacy. Thus, for example, one can begin applying the cream prior to encountering a known viral area such as an airplane. However, the cream has known cytotoxic effects (mediated through the cytokine production), especially if applied for weeks, so extended application would not be recommended. In the assay, TNF-a remained high for at least 6 h. In the treated group of macaques, the cream was washed away with warm water after the experiments. No animal had cytotoxic effects when examined at 6 h, 12 h, or 24 h, except one animal, which had an episode of lacrimation for 12 h post treatment. The cream needs to be applied to induce maximum concentration of IFN-a, but it may be removed when TNF-a continues to be elevated (after 6 h).

Figure 7:
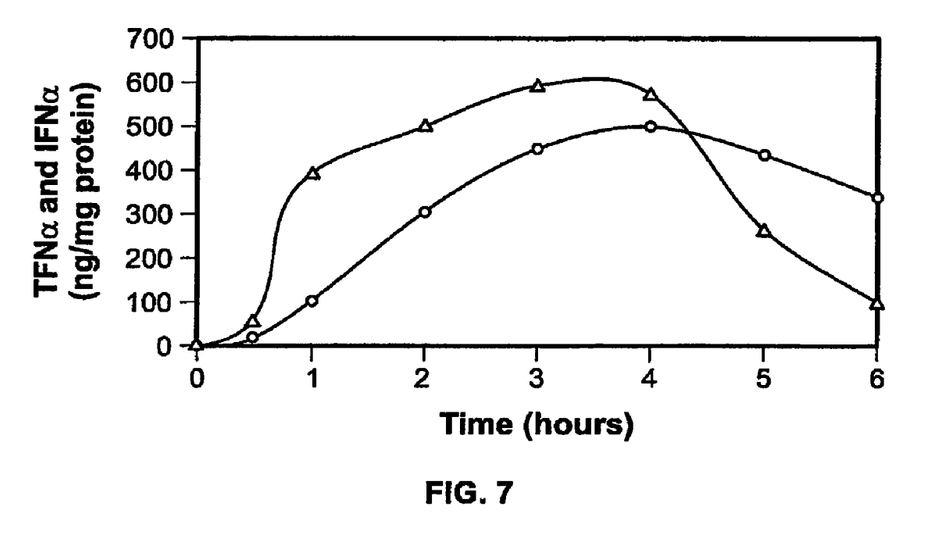
FIG. 7. shows the kinetics of cytokine induction by nasal application of imiquimod in macaques (n=4). ▲ IFN-a; ● TNF-a.
Figure 8:
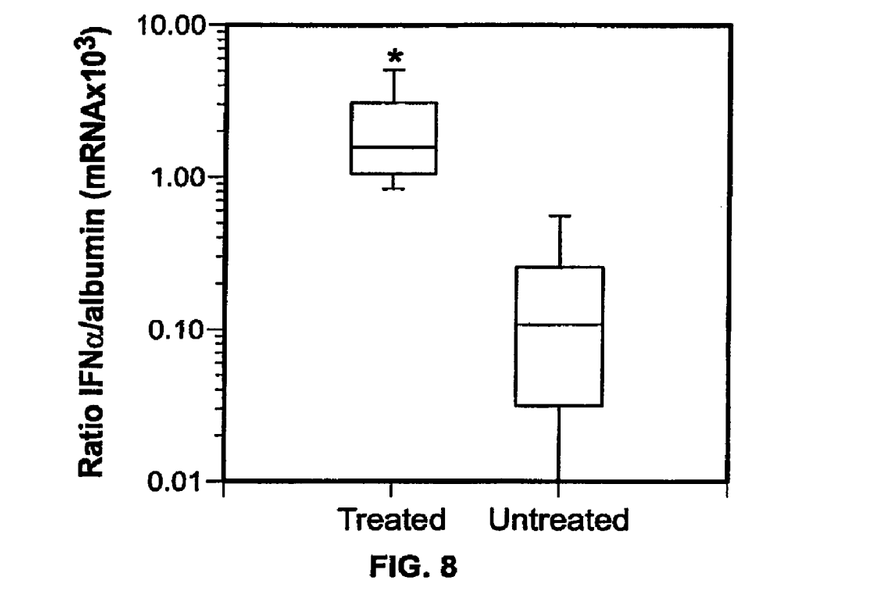
FIG. 8. shows intranasal expression of IFN-a mRNA by nasal application of imiquimod. Boxes show all results in a group. Medians indicated by horizontal bars; S.D. by vertical bars. Level of significance is given for mRNAs in relation to albumin mRNAs by using quantitative RT-PCR assays (p=0.004).

The assay also employed a second set of tests to evaluate mRNA IFN-a induction by imiquimod with postnasal swabs. mRNA was isolated and analyzed by quantitative competitive RT-PCR. An internal standard constructed to be complementary to and to compete with oligonucleotide primers and for amplification of target sequences was used. Samples taken 3-5 h after postnasal application were used. IFN-a protein expression was induced by imiquimod at levels 2-5 times the control samples. (FIG. 7) mRNA IFN-a was also variably induced in control animal samples (anesthesia only) at ratios between 0.01-0.55 with a median of 0.192. The treated animals expressed IFN-a protein at a level of 0.84-5.20 mRNA× $10^3$ with a mean of 2.3 IFN-a/albumin mRNA× $10^3$ (FIG. 3). The difference was significant (p=0.004) irrespective of whether IFN-a mRNA levels were related to albumin, 13 actin or GAPDH as reference transcripts.

To perform the assay, two groups of Indian Macaca mulatta verified to be free of simian immunodeficiency virus (SW) and simian retrovirus type D (SRV) infections were used. The control group (n=3) and the treated group (n=5) were sedated with glycopyrolate 0.01 mg/kg+acetaminophen 0.2 mg/kg and anesthetized with zolazepam (Telazol) 10 mg/kg intramuscular. The animals were then shaved under the nares and sample "0" from the postnasal fluid was taken by inserting thin sticks with cotton swabs deep into the nares. The swabs were then re-inserted in the sterile collection tubes containing transport media Hank's balanced salt solution with 10% glycerol and 200 U/mg each of penicillin and streptomycin, 250 mg/ml gentamycin and 50 U/mg nystatin. In the treatment group, ½ packet of Aldara™ cream was massaged gently in each naris. A packet of Aldara™ contains 0.25 g imiquimod and a base cream consisting of isostearic acid, cetyl alcohol, white petroleum, polyphorbate 60, glycerin, benzyl alcohol, and propylparaben. In the control group, only the cream was massaged. Samples were taken at different times and stored at 4° C. for 1 day and at −20° C. for one week. Physical examination after each sample and at 6 h, 12 h, and 24 h post anesthesia consisted of examining each macaque for fever, erythema, erosion, flaking, and lacrimation. The animals were followed for 1 week for change in weight, eating habits, stool consistency, and fever.

RNA was isolated with a high pure RNA isolation kit (Roche, Molecular Biochemicals) according to the instructions from the manufacturer.

Quantification by Competitive RT-PCR. Two mg total cellular RNA was reverse transcribed. Quantification of cDNA corresponding to transcripts of interest was performed by using internal cDNA standards (IS). In brief, IS were constructed to be complementary to and compete with oligonucleotide primers and for amplification of target sequences. Target cDNA were amplified in the presence of 10- and two-fold serial dilutions of the IS. The amount of target transcripts was then calculated on the basis of the known molecular quantity of the IS, and related to the amount of a reference mRNA (albumin, [3-actin, or glycerinaldehydephosphate dehydrogenase (GAPDH)), which had been quantified in parallel.[18,19]

IFN-a Primer Sequences

```
                                            SEQ ID NO: 1
    5'-GAAGCTTYCTCCTGYYTGAWGGACAGA-3'

SEQ ID NO: 2
    5'-GGG GA TCCTCTGACAACCTCCCANGCACA-3'
```

(annealing temperature 68; # cycles 36; mRNA size product 372 bp; IS size 506 bp).

Albumin Primers

```
                                            SEQ ID NO: 3
        5'-CTTGAATGTGCTGATGACAGG-3'

SEQ ID NO: 4
        5'-GCAAGTGAGCAGGCATCTCATC-3'
```

IFN-a and TNF-a enzyme-linked immunoabsorbent assays (ELISA). Levels of IFN-a and TNF-a were measured using commercially available multispecies kit (PBL Biomedical Laboratories) (product #41105-1). The range of detection was 10-500 pg/ml (high sensitivity protocol).

Statistical analysis. Data were compared using student t-test or one-way ANOVA and Dunnett's comparison test. Differences were considered significant at p<0.05.

A More powerful Imidazoquinolinamine is in the pipeline (e.g. Reziquimod). I expect it to be even more powerful as an antiviral agent for the same purposes.

I claim:

1. A method of increasing the time period between outbreaks of genital herpes consisting essentially of:
   providing an imidazoquinolinamine formulation;
   disposing an amount of the imidazoquinolinamine formulation into a first nare of an individual infected with Herpes Simplex Virus type 2;
   covering at least a portion of the internal surface of the individual's first nare with a portion of the amount of the imidazoquinolinamine in the first nare;
   massaging the portion of the amount of the imidazoquinolinamine into the internal surface of the first nare;
   disposing the amount of the imidazoquinolinamine formulation into a second nare of the individual;
   covering at least a portion of the internal surface of the second nare with a portion of the amount of the imidazoquinolinamine in said the second nare; and
   massaging the portion of the amount of the imidazoquinolinamine into the internal surface of said the second nare.

2. The method of claim 1, wherein the imidazoquinolinamine formulation's active ingredient is selected from the group consisting of imiquimod and resiquimod.

3. The method of claim 1, wherein the imidazoquinolinamine formulation is disposed using a device selected from the group consisting of a swab, syringe, spray nozzle, and a drip applicator.

4. The method of claim 3, wherein the device distributes the imidazoquinolinamine formulation over the internal surface of the first nare and over the internal surface of the second nare.

5. The method of claim 1, wherein the imidazoquinolinamine formulation comprises imiquimod as an active ingredient in the amount of about 12 mg.

6. The method of claim 1, wherein the imidazoquinolinamine formulation comprises resiquimod as an active ingredient in the amount of about 12 mg.

7. The method of claim 1, wherein the imidazoquinolinamine formulation is selected from a group consisting of a cream, gel, liquid, paste, aerosol, and an emulsion.

8. The method of claim 1, wherein about 15 minutes prior to disposing the imidazoquinolinamine formulation, the first nare and the second nare are treated with a decongestant.

9. The method of claim 8, wherein the decongestant is phenylephrine.

10. The method of claim 1, wherein the individual is infected with viral rhinitis.

11. The method of claim 1, wherein the imidazoquinolinamine formulation is first applied within twelve hours after an appearance of first symptoms.

12. The method of claim 11, wherein the imidazoquinolinamine formulation is applied every twelve hours after the first application.

13. The method of claim 12, wherein a total of four applications of the imidazoquinolinamine formulation are applied to the first nare and the second nare.

* * * * *